United States Patent
Hammerslag

[11] Patent Number: 5,820,592
[45] Date of Patent: Oct. 13, 1998

[54] ANGIOGRAPHIC AND/OR GUIDE CATHETER

[76] Inventor: Gary R. Hammerslag, P.O. Box 774807, Steamboat Springs, Colo. 80477

[21] Appl. No.: 680,789

[22] Filed: Jul. 16, 1996

[51] Int. Cl.⁶ .................................................. A61M 37/00
[52] U.S. Cl. ............................................. 604/95; 604/280
[58] Field of Search .............................. 604/280, 95, 281, 604/264; 128/657, 772; 600/139, 141, 143, 144, 146–152

[56] References Cited

U.S. PATENT DOCUMENTS

| | | | |
|---|---|---|---|
| 3,169,528 | 2/1965 | Knox, III et al. ...................... | 604/281 |
| 3,470,876 | 10/1969 | Barchilon . | |
| 3,605,725 | 9/1971 | Bentov . | |
| 4,299,226 | 11/1981 | Banka . | |
| 4,747,827 | 5/1988 | Micek ...................................... | 604/54 |
| 4,748,984 | 6/1988 | Patel . | |
| 4,758,221 | 7/1988 | Jureidini . | |
| 4,759,748 | 7/1988 | Reed . | |
| 4,781,682 | 11/1988 | Patel . | |
| 4,813,930 | 3/1989 | Elliott . | |
| 4,820,271 | 4/1989 | Deutsch . | |
| 4,822,345 | 4/1989 | Danforth . | |
| 4,834,709 | 5/1989 | Banning et al. ......................... | 604/170 |
| 4,898,577 | 2/1990 | Badger et al. . | |
| 4,909,787 | 3/1990 | Danforth . | |
| 4,920,980 | 5/1990 | Jackowski . | |
| 4,921,482 | 5/1990 | Hammerslag et al. . | |
| 4,925,445 | 5/1990 | Sakamato et al. ........................ | 604/95 |
| 4,934,340 | 6/1990 | Ebling et al. . | |
| 4,998,916 | 3/1991 | Hammerslag et al. . | |
| 5,030,204 | 7/1991 | Badger et al. . | |
| 5,098,412 | 3/1992 | Shiu . | |
| 5,114,403 | 5/1992 | Clarke et al. ............................. | 604/96 |
| 5,122,125 | 6/1992 | Deuss . | |
| 5,131,406 | 7/1992 | Kaltenbach . | |
| 5,269,752 | 12/1993 | Bennett .................................... | 604/28 |
| 5,290,229 | 3/1994 | Paskar . | |
| 5,295,962 | 3/1994 | Crocker et al. . | |
| 5,306,245 | 4/1994 | Heaven . | |
| 5,308,342 | 5/1994 | Sepetka et al. . | |
| 5,334,145 | 8/1994 | Lundquist et al. . | |
| 5,352,197 | 10/1994 | Hammersmark et al. ............... | 604/95 |
| 5,368,566 | 11/1994 | Crocker et al. . | |
| 5,378,234 | 1/1995 | Hammerslag et al. . | |
| 5,391,146 | 2/1995 | That et al. . | |
| 5,395,328 | 3/1995 | Ockuly et al. . | |
| 5,397,321 | 3/1995 | Houser et al. ............................ | 604/95 |
| 5,415,633 | 5/1995 | Lazarus et al. . | |
| 5,421,826 | 6/1995 | Crocker et al. . | |
| 5,439,006 | 8/1995 | Brennen et al. . | |

FOREIGN PATENT DOCUMENTS

| | | |
|---|---|---|
| 0454264A1 | 10/1991 | European Pat. Off. . |
| 990417 | 9/1951 | France . |
| 3920707A1 | 1/1991 | Germany . |

*Primary Examiner*—Wynn Wood Coggins
*Assistant Examiner*—Deborah Blyveis
*Attorney, Agent, or Firm*—Knobbe, Martens, Olson & Bear, LLP

[57] ABSTRACT

The invention provides a guide catheter comprising an elongate tubular body having a proximal end and a distal end, and at least one central lumen extending axially therethrough. At least one torque control wire extends axially therethrough. In one embodiment, an actuator is connected to the torque control wire. Torquing the actuator results in steering or aiming the guide catheter. In another embodiment, a deflection wire extends through the catheter body. Manipulation of a control on the deflection wire deflects a distal portion of the deflection wire.

9 Claims, 5 Drawing Sheets

U.S. Patent     Oct. 13, 1998     Sheet 1 of 5     5,820,592
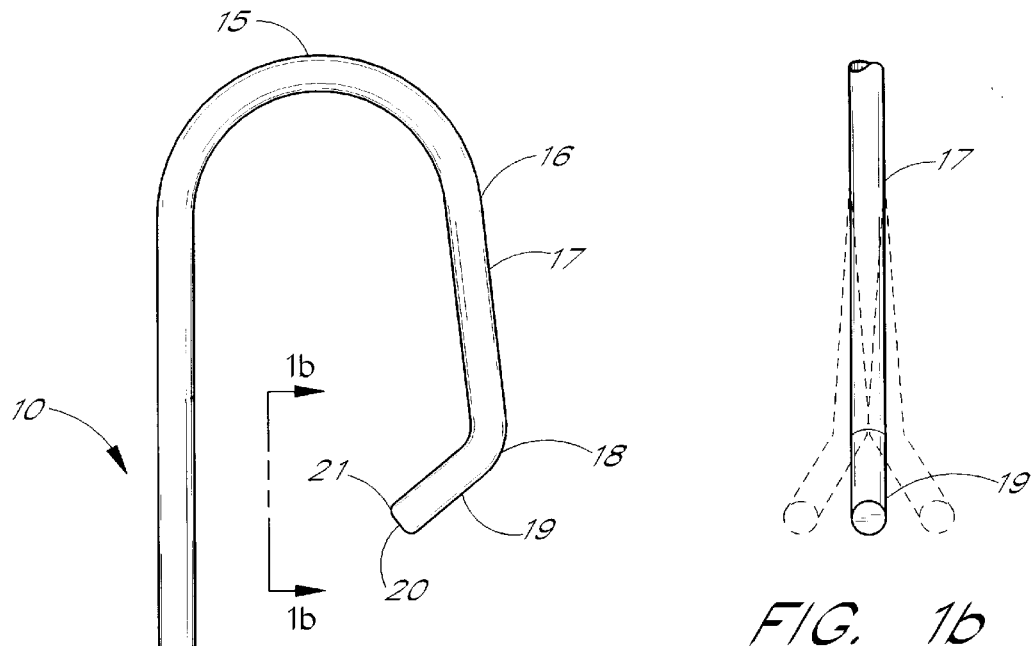
FIG. 1b
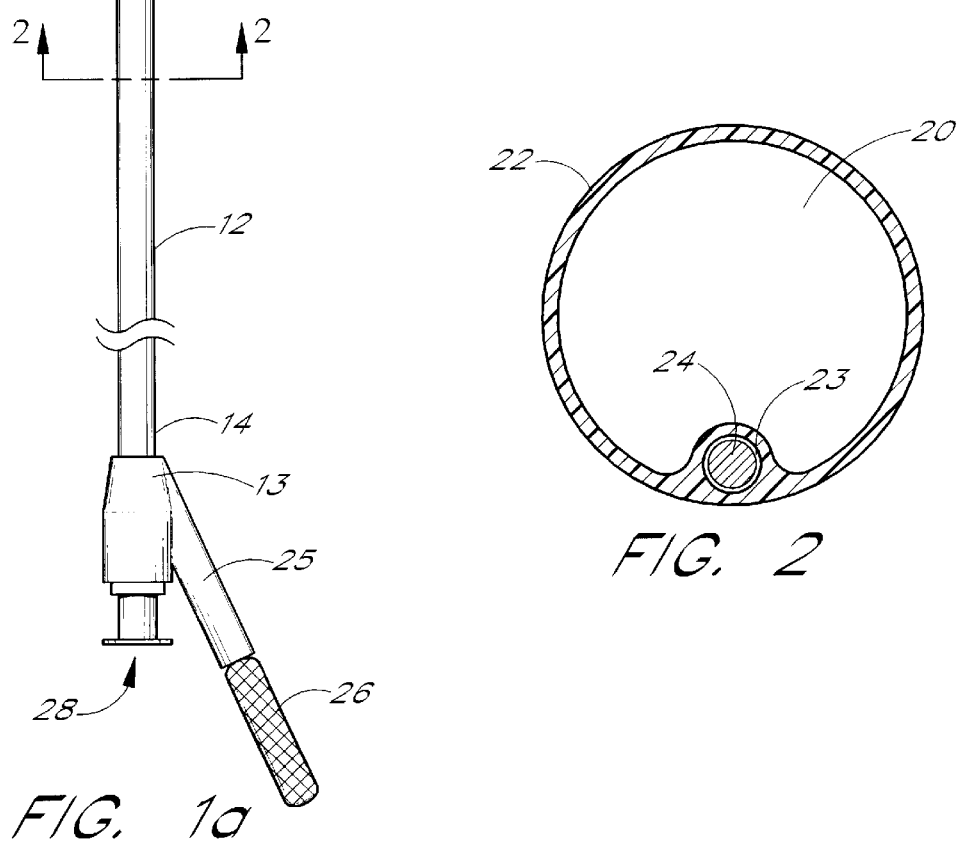
FIG. 1a
FIG. 2

ANGIOGRAPHIC AND/OR GUIDE CATHETER

FIELD OF THE INVENTION

This invention generally relates to catheters such as angiographic catheters or guide catheters for the placement of intracoronary devices within a patient's vascular system.

BACKGROUND OF THE INVENTION

Percutaneous transluminal coronary angioplasty (PTCA) requires manipulation of a catheter from a position outside a patient's body through extended portions of the patient's arterial system to a stenotic site for the purposes of alleviating a lesion by inflating a balloon. This particular procedure, performed with increasing frequency over the past several years, is often done in preference to open heart bypass surgery.

In addition to PTCA, a growing variety of other diagnostic and therapeutic catheterizations also require or are facilitated by an elongate flexible tubular catheter. For example, angiographic catheters are a frequently used form of diagnostic catheter, for delivering a radiopaque dye to an arterial site. Catheters built in accordance with certain embodiments of the present invention are particularly useful for angiographic applications.

In a typical angioplasty procedure, a guide catheter is percutaneously introduced into the femoral artery of the patient and advanced until the distal tip is in the ostium of the desired coronary artery. A guidewire is then advanced through the guide catheter into the patient's coronary vasculature until the distal end of the guidewire crosses the lesion to be dilated. A dilatation catheter having an expandable distal balloon is advanced over the previously introduced guidewire until the dilatation balloon is properly positioned across the lesion. Once in position across the lesion, the balloon is inflated to a predetermined size with radiopaque liquid at relatively high pressures (e.g., generally 4–12 atmospheres). The inflated balloon compresses and/or splits the atherosclerotic plaque of the lesion against the inside of the artery wall to thereby restore patency to the lumen. The balloon is then deflated so that the dilatation catheter can be proximally withdrawn and blood flow resumed through the dilated artery.

Guide catheters or angiographic catheters are generally provided with one or more preset angles or radiused curves which are customized to provide access to particular coronary anatomies. Guide catheters configured, for example, to assist in the placement of a catheter in the left coronary artery must be designed in a manner that permits transluminal advance from the percutaneous access site over the aortic arch and to the ostium of the left coronary artery. See, for example, FIG. 1 in U.S. Pat. No. 4,822,345 to Danforth.

Due to anatomical variations, the fixed preset guide catheters are not always able to provide an optimal entrance angle into the desired artery. The takeoff angle and position of any particular branch artery varies from patient to patient, normally making it desirable to have a selection of different guide catheters on hand for a catheterization procedure. Other prior art efforts to improve guide catheter performance have included catheters having a control at the proximal end which can adjust the radius of curvature of the distal bend. See, for example, U.S. Pat. No. 4,898,577 to Badger et al. Through a combination of torquing the end of the catheter and pulling the pull wire to affect the distal bend, the Badger catheter is said to provide advantages in positioning the distal end of the catheter within difficult to reach coronary ostia.

While use of a pull wire to deflect the tip of a catheter may be effective in bending the tip, the deflection of the steerable catheter tip of the Badger et al design occurs in only a single plane. This design, as well as the design disclosed in Danforth, still relies upon the torqueability of the catheter for proper placement.

Unfortunately, torque transmission has not been perfected in the prior art. Due to the length of the tubular body between the proximal control end and the pre-bent distal tip, torsion can tend to accumulate as the proximal end of the catheter is twisted to rotate the tip. The accumulated torsional moment may release unevenly, resulting in skipping or rapid rotation of the distal tip inside the vessel. The rapid rotation may damage the blood vessel walls and/or cause overshooting of a branch vessel entrance which will add time to the placement procedure.

To optimize torque transmission, the wall of the prior art guide catheters generally comprises a series of layers. In a typical guide catheter, a woven metal or polymeric tubular braid may be sandwiched between an inner tubular sleeve and an outer tubular jacket. See, for example, the configurations illustrated at FIGS. 3 and 4 in U.S. Pat. No. 4,898,577 to Badger et al. As a consequence, improved torqueability generally results in increased wall thickness, which in turn increases the outside diameter of the guide catheter for any given desired inside diameter. In general, it is desirable in coronary arterial applications as well as other vascular applications in the body to maximize the ratio of the inside diameter of any functional lumen to the outside diameter of the tubular body.

Accordingly, there remains a need for a steerable guide or angiographic catheter having a structure that permits controllable positioning of the catheter tip throughout a useful range and which has optimal torque transmission, column strength and a minimal wall thickness. Preferably, the shape of the catheter can also be manually adjusted by the clinician at the time of the procedure such as by manually bending to the desired configuration.

SUMMARY OF THE INVENTION

There is provided in accordance with one aspect of the present invention a catheter, comprising an elongate tubular body having a wall, a proximal end and a distal end. At least one central lumen extends axially throughout the tubular body. At least one rotatable wire extends axially through the tubular body and a proximal actuator is provided on the tubular body and in connection with the wire. Manipulation of the actuator to rotate the wire results in steering of the distal end of the catheter.

In accordance with another aspect of the present invention, there is provided a catheter comprising an elongate flexible tubular body having a wall, a proximal end and a distal end. At least one central lumen extends axially throughout the tubular body. At least one wire also extends axially through the tubular body. The tubular body is manually bendable and the wire retains a set if the tubular body is manually bent.

In one embodiment, the wire comprises an outer cylindrical housing having a central lumen extending therethrough and an inner core wire axially movably positioned within the lumen. Proximal axial displacement of the core wire with respect to the cylindrical housing causes a lateral displacement of the cylindrical housing which in turn causes a lateral displacement of a portion of the catheter.

In accordance with a further aspect of the present invention, there is provided a steerable guide or angiographic catheter. The catheter comprises an elongate flexible tubular body having a proximal end, a distal end, and at least one central lumen extending axially therethrough. An elongate flexible deflection element extends through the body, the deflection element comprising a first and second axially extending component. Axial displacement of the first component relative to the second component causes a lateral deflection at a predetermined point along the catheter.

In accordance with a further aspect of the present invention, there is provided a method of negotiating a patient's arterial system with a catheter. The method comprises the steps of introducing the catheter into the patient's arterial system, wherein the catheter comprises an elongate tubular body having a proximal end and a distal end and at least one preset curve, at least one central lumen and at least one torque control wire extending axially therethrough. The catheter is advanced distally through the arterial system, and the catheter is aimed into the ostium of a branch artery by manipulating the torque control wire to steer and or aim the distal end of the catheter.

In accordance with a further aspect of the present invention, there is provided a method of positioning an angiographic or guide catheter within a target site in a patient's vascular system. The method comprises the steps of providing a catheter of the type having an elongate flexible tubular body having proximal and distal ends, a central lumen extending axially throughout and at least one wire extending axially through the wall of the catheter. The distal end of the catheter is positioned within the patient's vascular system, and the catheter is advanced distally through the patient's vascular system by applying a distal force to a proximal portion of the catheter. A substantial portion of the force is transmitted along the catheter to the distal end of the catheter by way of the wire to advance the catheter to the treatment site. The wall thickness of the catheter is sufficiently thin that the catheter would lack sufficient column strength to reach the target site if the wire were not present.

Further features and advantages of the present invention will become apparent to those of skill in the art in view of the detailed description of preferred embodiments which follows when considered together with the attached drawings and claims.

BRIEF DESCRIPTION OF THE DRAWINGS

FIG. 1a is a schematic view of a catheter according to the present invention.

FIG 1b illustrates a range of motion of the distal tip in response to rotation of the torque knob on the embodiment of FIG. 1a.

FIG. 2 is a cross-sectional view taken along line 2—2 of FIG 1.

DETAILED DESCRIPTION OF THE PREFERRED EMBODIMENTS

Figure 1C:
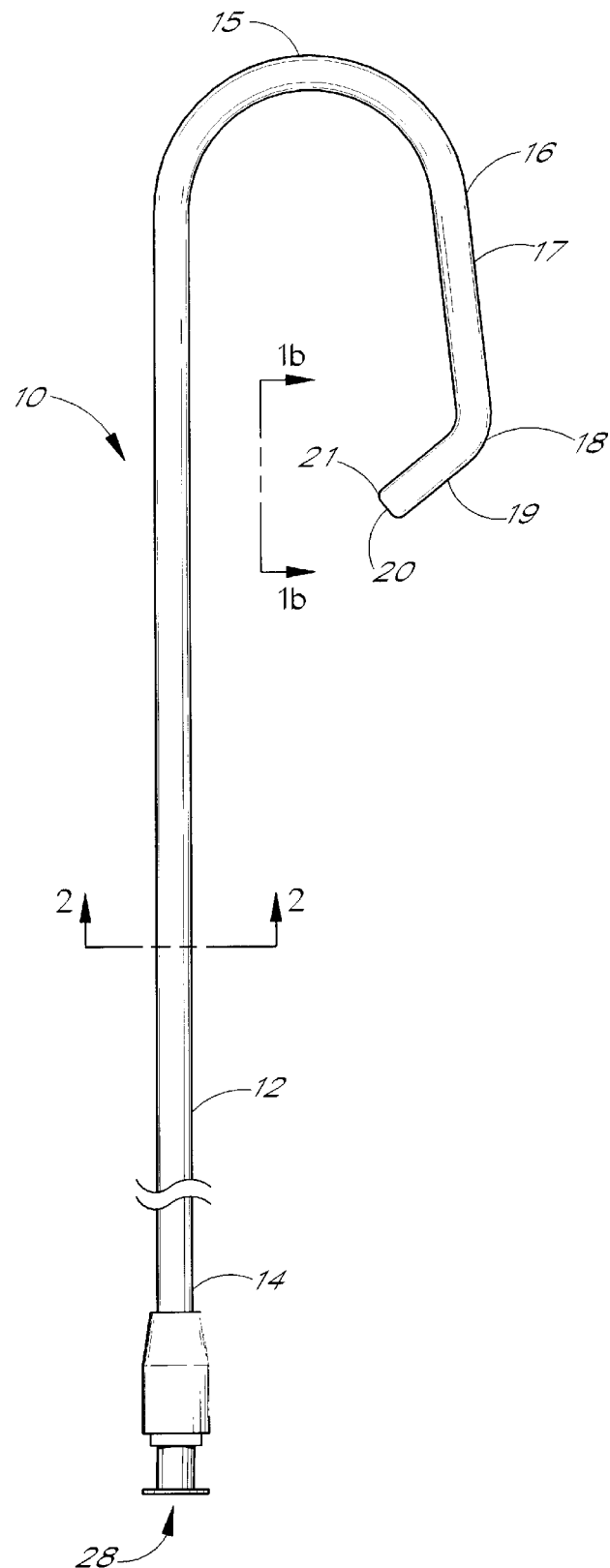
FIG. 1c is an alternate embodiment of a catheter in accordance with the present invention.

As illustrated in FIG. 1, a guide or angiographic catheter 10 in accordance with the present invention comprises an elongate tubular body 12 having a proximal end 14 and a distal end 16. Although described herein primarily in the context of guide catheters, it is to be understood that the present invention is useful for a wide variety of diagnostic and therapeutic purposes which require placement of a tubular access catheter.

The distal end 16 generally comprises a radiused first curve 15, disposed proximally of a relatively linear segment 17. The segment 17 is disposed proximally of a second bend 18. Second bend 18 is spaced apart from the distal tip 21 of guide catheter 10 by a relatively short distal segment 19.

In a typical guiding catheter of the present invention configured for introduction into the femoral artery for use in a conventional left coronary artery dilatation, the elongate tubular body 12 has an axial length within the range of from about 65 cm to about 125 cm. The tubular body 12 is provided with a customized preset curvature such as that illustrated in FIG. 1a. Notwithstanding the preset curvature, the tubular body 12 is sufficiently flexible that it can be straightened for the purpose of percutaneous insertion and transluminal advance towards the coronary artery. The preset provides a lateral bias at the distal tip of the tubular body 12, for aiming the catheter and seating the distal tip in the desired ostium as is well understood in the art.

The first curve 15 is biased or preset such that, in an unconstrained or relaxed configuration it has a generally constant radius of curvature within the range of from about 10 mm to about 30 mm. The proximal limit of the curve 15 commences within the range of from about 55 cm to about 120 cm from the proximal end 14 of the catheter. The arc length of the first curve 15 is such that the relatively linear segment 17 is positioned nearly parallel to the elongate tubular body 12 proximally of the first curve 15. Segment 17 has a generally linear length within the range of from about 1 cm to about 6 cm. Second bend 18 has a relatively shorter radius of curvature than the radius of first curve 15. In the illustrated embodiment, second bend 18 has a radius within the range of from about 3 mm to about 10 mm. The arc length of second bend 18 is sufficient to project distal segment 19 at about a 45° angle with respect to the longitudinal axis of segment 17.

Although the first curve 15 is preferably preset as illustrated in FIGS. 1a and 1c, the catheter of the present invention is preferably also manually formable by the clinician at the clinical site. Thus, the torque wire 24 or the spline such as in the embodiment illustrated in FIG. 1c are bendable so that the clinician can prebend the catheter prior to introduction, or withdraw the catheter during the procedure and reshape the distal curvature to improve navigation of the arterial system and enhance aiming at the desired ostium as will be discussed.

The precise axial lengths, diameters and curvature configurations can be varied widely within the scope of the present invention, depending upon the desired application of the guide catheter and the particular anatomy encountered in a given patient. In addition to the left Judkin's configuration described above, guiding catheters of the present invention can be readily configured for other configurations of guiding catheters such as the Judkin's, Stone's, Stertzer, Amplatz or other configurations as will be understood to those of skill in the art in view of the disclosure herein.

The proximal end 14 of the embodiment of guiding catheter 10 illustrated in FIG. 1a, is provided with a manifold 13. Manifold 13 is provided with a proximal access port 28, for providing access to an elongate central lumen 20. Manifold 13 is further provided in one embodiment with a sidearm 25 for supporting a rotatable torquing knob 26. Manifold 13 can be produced by injection molding techniques well known in the art.

Torquing knob 26 is rotationally coupled to an elongate flexible torque wire 24. Torque wire 24 can comprise any of a variety of materials and designs sufficient to transmit a desirable level of torque to the distal end of the guide catheter. Torque wire 24 also contributes to the pushability of the guide catheter of the present invention. Woven or braided multi-filament materials such as polymers or metal wire may be used. Preferably, the torque wire 24 is a single strand metal wire or rod. In one embodiment, the torque wire 24 comprises a stainless steel rod having an outside diameter of about 0.020 inches in an 8 French guide catheter. Alternatively, the torque wire 24 comprises a hollow element such as a section of without a central core wire as will be discussed.

As illustrated in FIG. 2, the elongate tubular body 12 preferably has a single layer wall 22 which defines central lumen 20 extending axially therethrough. Wall 22 is preferably provided with a torque wire lumen 23 for receiving torque wire 24 axially therethrough. Preferably, torque wire lumen 23 extends substantially the entire length of the tubular body 12. In this manner, the torque wire lumen 23 is isolated from the central lumen 20. Alternatively, torque wire lumen 23 may extend for only portions of the axial length of the tubular body 12, such as in intended-use applications where exposure of the torque wire 24 to the central lumen 20 is acceptable. As a further alternative, the guide or angiographic catheter is a single-lumen catheter having both the torque wire 24 and the working catheter and/or injected dye extending through the same central lumen.

In an alternate embodiment, illustrated in FIG. 1c, the sidearm 25 and torquing knob 26 are omitted. In this embodiment, in place of a torque wire 24 there is provided an elongate flexible metal spline or support wire. The spline permits manual deformation of the distal configuration of the catheter 10, which may be desirable during placement procedures as will be appreciated by those of skill in the art.

The spline extending through catheter 10 in the embodiment illustrated in FIG. 1c is still capable of transmitting catheter torque from the proximal end to the distal end such as during placement, as well as providing column strength to the catheter 10. This enables elimination of the multi-layer wall known in the prior art. In this embodiment, the inside diameter is increased for a given outside diameter compared to the prior art. For example, a 5 French diagnostic catheter constructed in accordance with the embodiment of FIG. 1c has been determined by the present inventor to be able to deliver about the same amount of radiopaque dye as a 6 French multilayer wall prior art catheter. This is due to the larger effective inside diameter of the catheter, which is available as a result of thinning the wall thickness and transferring column strength structural support from the wall to the internal spline.

Although the invention is illustrated having only a single layer wall 22, multiple layer walls can also be used as will be apparent to those of skill in the art. In general, one advantage of the present invention is optimized by providing a thin, single layer wall 22 to optimize flexibility and the inside diameter of the central lumen 20. In one preferred embodiment, the guide catheter has an outside diameter of 0.105 inches (8 French) and a wall thickness of about 0.005 inches. The torque wire has a diameter of about 0.020 inches and the diameter of the central lumen 20 taken along an axially extending plane which runs through the center of torque wire 24 is about 0.075 inches (Vertical dimension of FIG. 2). The inside diameter of lumen 20 taken along the horizontal in FIG. 2 is about 0.095 inches.

Elongate tubular body 12 can be manufactured in accordance with any of a variety of techniques known in the art. For example, the tubular body 12 may comprise a dual lumen extrusion of any of a variety of well known medical grade catheter polymers. Suitable polymers include high and medium density polyethylene, as well as a variety of other materials such as Pebax and others that are well known in the art. Alternatively, the catheter body 12 can be manufactured as a coextrusion, with the torque wire positioned therein.

In one embodiment in accordance with FIG. 1a, the torque wire 24 is rotatable within the lumen 23 throughout most of the length of the catheter. Due to the pre-bent configuration of the torque wire 24 at about second bend 18, rotation of torque control 26 will produce a steering effect with respect to distal tip 21, as illustrated in FIG. 1b.

In the embodiment illustrated in FIG. 1a, the torque wire 24 will normally have a circular cross-sectional configuration. However, oval or flat (ribbon shaped) wires may alternatively be used, provided that the resulting torquing characteristics are suitable for the intended use application. Oval or rectangular cross-sectional splines may be particularly suited for use in a embodiment such as that illustrated in FIG. 1c, where rotation of the spline with respect to the body of the tubular catheter 10 is unnecessary. Rectangular splines having cross-sectional dimensions within the range of from about 0.010 inches to about 0.030 inches by about 0.020 inches to about 0.040 inches may be utilized in the context of a 5 French catheter, however, other dimensions may readily be incorporated into catheters without departing from the teachings of the present invention.

Figure 3:
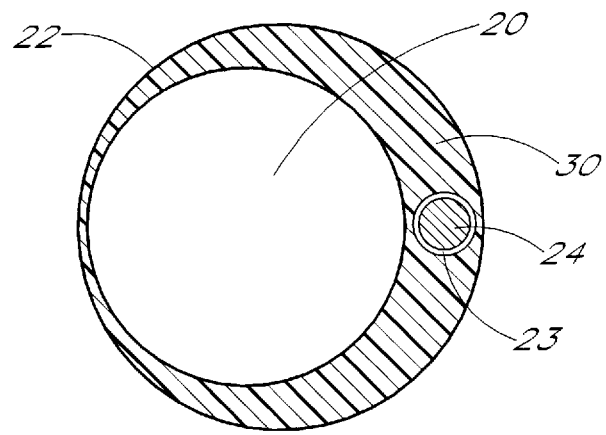
FIG. 3 is a cross-sectional view taken along line 2—2 of FIG. 1 illustrating an alternate embodiment of a catheter in accordance with the present invention.

FIG. 3 is a cross-sectional view of an alternative embodiment of a guide catheter 10 in accordance with the present invention. The elongate tubular body 12 has a single layer wall 22 with a central lumen 20 extending axially therethrough. In this embodiment, the central lumen 20 has the largest practical circular cross section that will fit within the constraints imposed by torque control wire 24. The central lumen 20 is positioned eccentrically within the elongate tubular body 12, and the thickness of single layer wall 22 increases to a sufficient thickness to accommodate lumen 23, wherein the torque control wire 24 is disposed.

Figure 6:
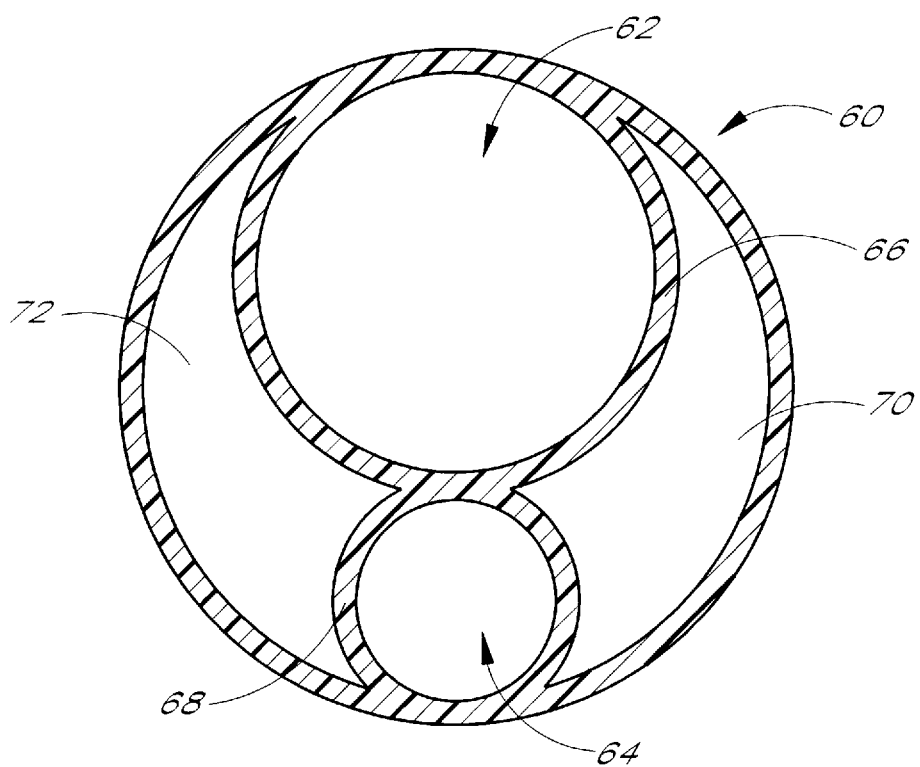
FIG. 6 is a cross-sectional view of an alternate extrusion profile for a catheter in accordance with the present invention.

FIG. 6 is a cross-sectional view of a further alternative embodiment for the guide catheter extrusion. In this embodiment, an outer catheter wall 60 encloses a catheter lumen 62 and a spline lumen 64. The catheter lumen 62 is defined within a first interior wall 66, and the spline lumen 64 is defined by a second interior wall 68. The cooperation of the first interior wall 66 and second interior wall 68 provides a first dye lumen 70 and a second dye lumen 72.

In one embodiment, the outer catheter wall 60 and each of the first and second interior walls 66 and 68 have a wall thickness in the area of about 0.003 inches. The outside diameter of the catheter body is 7 French, or about 0.092 inches. The inside diameter of the catheter lumen 62 is about 0.053 inches, and the inside diameter of the spline lumen 64 is about 0.030 inches. In this embodiment, the combined area of the catheter lumen 62 and dye lumens 70 and 72 are on the order of about 13% larger than the corresponding area of a 0.070 inside diameter conventional guide catheter. As will be appreciated by those of skill in the art in view of the disclosure herein, the use of the spline in the catheter of the present invention permits a wide variety of alternate extrusion profiles which will provide a relatively high total cross-sectional interior area relative to the outside diameter of the catheter, as compared to the prior art.

Figure 4:
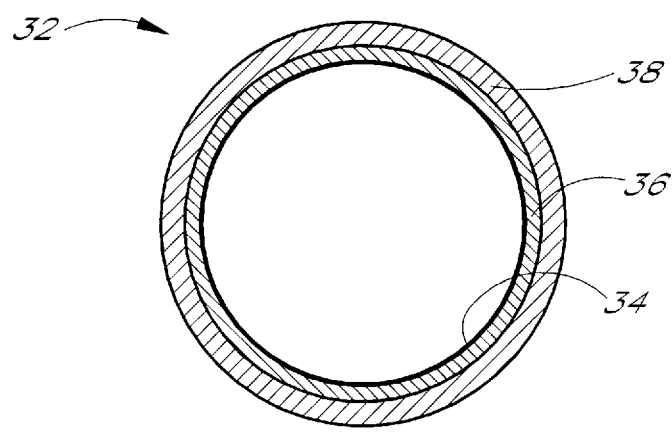
FIG. 4 is a cross-sectional view of a standard prior art guide catheter having a multi-layer wall.

A representative prior art multi-layer wall guide catheter 32 having multiple layer walls to provide torque and column strength is illustrated in FIG. 4. The multiple layers are usually composed of a lubricous inner layer 34, a middle layer of metal or fiber braid 36 to enhance torque transmission, and an outer layer 38 to provide more body and to encase the braided middle layer. A conventional 8 French multi-layer wall guide catheter has an outside diameter of 0.105 inch. It has a wall thickness of about 0.0095 inch. It therefore has an inside diameter on the order of 0.086 inch.

By contrast, in the splined guide catheter of the present invention, the primary torque transmission and pushability properties are transferred from the catheter wall to the spline or torque control wire 24 disposed in or adjacent to the catheter wall. The balance of the catheter wall can therefore be relatively thin. In a preferred embodiment, it is a single layer wall. A wall thickness of 0.002 to 0.010 inch is contemplated, while 0.005 inch is preferred in a wall comprising Pebax. The advantage of this design is that the inside cross sectional area, discounting the diameter of the spline (0.020 inch), is much greater for a given outside diameter because of the decreased wall thickness. For example, given an outside diameter of the order of 0.095 inch. Consequently, for a given outside diameter, a larger inside diameter is available for work compared to the prior art.

Another advantage of the present invention is improved torque transmission. Torque is transmitted through the torque control wire 24 rather than the wall of the catheter tube. Torque transmission will approach that of a guidewire. A further advantage of the present invention is that, in contrast to conventional catheters that are expensive to build because of the requirement for multi-layer walls, the present invention will be relatively inexpensive by virtue of its having a single layer wall.

In accordance with a further aspect of the present invention, there is provided a spline or torque wire which permits controlled deflection of the catheter. Preferably, the deflection spline is positioned to permit controlled deflection at the second bend 18 to facilitate aiming of the distal end 21 at the appropriate ostium. In addition, the deflectable spline permits adjustment of the launch angle from the guide catheter into the ostium, the desirability of which will be well understood to those of skill in the art.

Figure 5:
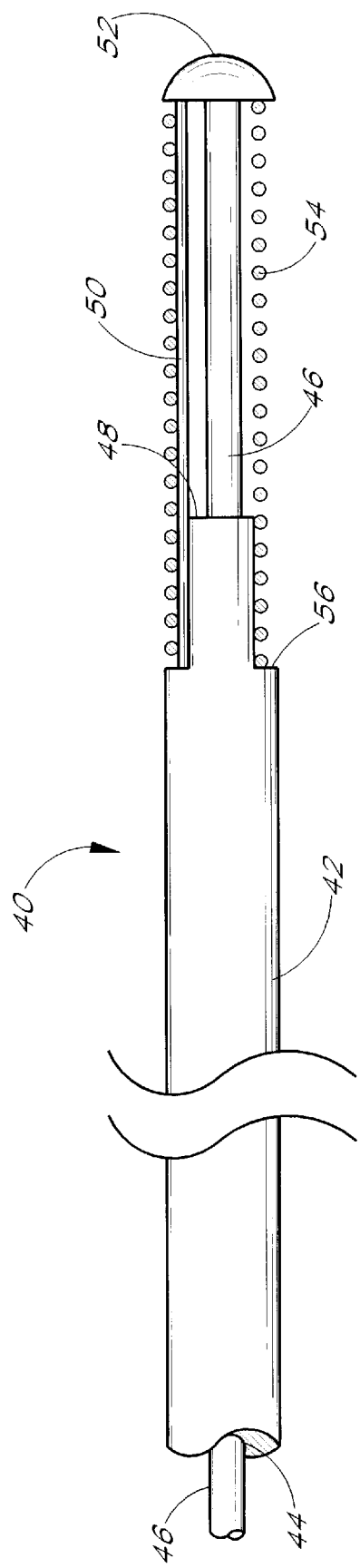
FIG. 5 is an enlarged cross-sectional elevational view of the distal end of a deflectable torque wire in accordance with the present invention.

Referring to FIG. 5, there is illustrated a partial cross-sectional view of the distal end of a deflection spline 40 which can be used in place of the torque wire 24 in a embodiment such as that illustrated in FIG. 1a, or in place of the spline such as that which would be utilized in an embodiment such as that illustrated in FIG. 1c. The deflection spline 40 comprises a tubular housing 42 such as a length of hypodermic needle tubing. In one embodiment, hypodermic tubing having a 0.020 inch outside diameter and a 0.007 inch inside diameter has been used. The tubing 42 is provided with a central lumen 44 for slidably receiving a core wire 46. Core wire 46 is connected to a proximal control (not illustrated) for controllably advancing the core wire 46 distally or retracting the core wire 46 proximally to control the distal tip. In one embodiment, the core wire 46 comprises a 0.006 inch diameter stainless steel wire.

The hypotube 42 is provided with a distal end 48 which is spaced apart from the distal end of the deflection spline 40 in the illustrated embodiment by about 7 mm. Core wire 46 extends distally from the distal end 48 of hypotube 42 and terminates in a distal tip 52. A support such as a reference ribbon 50 extends distally from the hypotube 42 to the distal tip 52. Preferably, reference ribbon 50 has a sufficient column strength that upon proximal retraction of core wire 46, the reference ribbon 50 will not collapse but will instead cause the distal tip to deflect in the direction of the core wire 46. In one embodiment, the reference ribbon 50 comprises a 0.003 inch by 0.010 inch flat stainless steel ribbon.

In one embodiment, the distal region of the deflection spline 40 is provided with a tubular housing such as spring coil 54. The distal end of the hypotube 42 may be provided with an annular shoulder 56 for receiving the proximal end of spring coil 54 with a minimal or no interruption of the outside profile of the completed assembly. In one embodiment, the spring coil 54 comprises a 0.020 inch outside diameter by 0.012 inch inside diameter coil of 0.004 inches diameter wire. Additional details of a suitable steering mechanism are disclosed in U.S. Pat. No. 3,521,620 to Cook, the disclosure of which is hereby incorporated by reference.

In accordance with one method of use, a percutaneous transluminal procedure, such as PTCA or other therapeutic or diagnostic procedure, is performed. First, the guide catheter is inserted through the femoral artery and advanced transluminally into the patient's aorta. Next, the distal tip of the guide catheter is maneuvered into the ostium of the desired coronary artery. Maneuvering is accomplished by torquing the torque knob 26 as the guide catheter is advanced distally. Preferably, the entire polymeric portion of the tubular body is provided with Barium to render the catheter radiopaque to facilitate visualization if desired.

If placement is difficult due to the anatomy of the patient, the catheter can be proximally withdrawn and the distal end manually prebent by the physician. The catheter can then be reintroduced into the patient and manipulated to the placement site. In an embodiment in accordance with FIG. 1, rotation of torque knob 26 accomplishes a translation of the distal tip 21 to facilitate aiming of the distal tip into the appropriate ostium. Alternatively, in an embodiment which incorporates the deflection spline 40 (FIG. 5), the proximal control can be manipulated to aim the distal tip of the catheter into the desired ostium, and to adjust the angle of the distal tip to optimize the launch angle from the catheter into the coronary artery.

A working catheter is then passed through the guide catheter, typically over or alongside a guidewire, into the artery. The catheter is advanced through the artery until the working catheter is located within the stenotic lesion or other desired target site.

Preferably, different degrees of flexibility are present along the length of torque control wire 24. Differing degrees of flexibility, particularly at the pre-bent distal tip, allows the catheter to be more flexible at the distal end 16 of the catheter. More flexibility at the distal end 16 permits fitting the catheter to the anatomy of the patient better. Flexibility can be affected by using different materials for the proximal and distal portions of the torque control wire 24 (materials having about the same dimensions), or by using the same materials but having different dimensions. For example, regions of the torque control wire 24, particularly the distal portion, can be tapered, or altered by scoring or cutting of ridges.

Although this invention has been described in terms of certain preferred embodiments, other embodiments that are apparent to those of ordinary skill in the art are also within the scope of this invention. Accordingly, the scope of the invention is intended to be defined only by reference to the appended claims and equivalents thereof.

What is claimed is:

1. A catheter, comprising:

an elongate flexible tubular body having a wall, a proximal end and a distal end, at least one central lumen extending axially therethrough, and at least one wire extending axially therethrough, at least a portion of said wire being fixed along its length to said tubular body so that rotation of the wire applies torque to the tubular body;

wherein the tubular body is manually bendable and the wire retains a set if the tubular body is manually bent.

2. A catheter as in claim 1, wherein said elongate flexible tubular body comprises a single layer wall.

3. A catheter as in claim 2, wherein the wire extends axially through the single wall.

4. A catheter as in claim 1, wherein said wire comprises an outer cylindrical housing having a central lumen extending therethrough, and an inner core wire axially movably positioned within the lumen.

5. A catheter as in claim 4, wherein said cylindrical housing has a distal end, and further comprising an axially extending support extending in a distal direction from the distal end of the cylindrical housing the support axially fixed with respect to the core wire such that proximal displacement of the core wire laterally displaces at least a portion of the support.

6. A catheter, comprising:

an elongate flexible tubular body having a wall, a proximal end and a distal end, at least one central lumen extending axially therethrough;

at least one wire extending axially through the tubular body, said wire comprising an outer cylindrical housing having a distal end and a central lumen extending therethrough, and an inner core wire axially movably positioned within the lumen; and an axially extending support extending in a distal direction from the distal end of the cylindrical housing, the support axially fixed with respect to the core wire such that proximal displacement of the core wire laterally displaces at least a portion of the support;

wherein the tubular body is manually bendable and the wire retains a set if the tubular body is manually bent.

7. A catheter as in claim 6, wherein said elongate flexible tubular body comprises a single layer wall.

8. A catheter as in claim 7, wherein the wire extends axially through the single wall.

9. A steerable guide or angiographic catheter comprising:

an elongate flexible tubular body having a proximal end, a distal end, and at least one central lumen extending axially therethrough;

at least one wire extending axially through the tubular body, said wire being fixed with respect to the tubular body wherein rotation of said wire results in rotating the distal end of said catheter;

an elongate flexible deflection element extending through the tubular body, said deflection element comprising first and second axially extending components;

wherein proximal advancement of the first component relative to the second component causes a lateral deflection of the distal end.

* * * * *